United States Patent
Jadhav et al.

(10) Patent No.: US 9,204,629 B2
(45) Date of Patent: Dec. 8, 2015

(54) AGRICULTURAL PESTICIDE FORMULATIONS AND PROCESS FOR MAKING THE SAME

(75) Inventors: Prakash Jadhav, Mumbai (IN); Jaidev Rajnikant Shroff, Dubai (IN)

(73) Assignee: UPL Limited, Mumbai (IN)

( * ) Notice: Subject to any disclaimer, the term of this patent is extended or adjusted under 35 U.S.C. 154(b) by 282 days.

(21) Appl. No.: 12/775,888

(22) Filed: May 7, 2010

(65) Prior Publication Data

US 2011/0275710 A1  Nov. 10, 2011

(51) Int. Cl.
*A01N 25/08* (2006.01)
*A01N 25/12* (2006.01)

(52) U.S. Cl.
CPC ............... *A01N 25/08* (2013.01); *A01N 25/12* (2013.01)

(58) Field of Classification Search
None
See application file for complete search history.

(56) References Cited

U.S. PATENT DOCUMENTS

| 2006/0014724 | A1* | 1/2006 | Jadhav et al. | 514/65 |
| 2008/0171661 | A1* | 7/2008 | Misselbrook | 504/136 |
| 2008/0312320 | A1* | 12/2008 | Shroff et al. | 514/529 |
| 2009/0197765 | A1* | 8/2009 | Gaytan et al. | 504/130 |
| 2009/0305889 | A1* | 12/2009 | Cush | 504/101 |

OTHER PUBLICATIONS

ChemicalBook entry [downloaded from www.chemicalbook.com/CASEN_82657-04-3.htm on Apr. 8, 2013].*

* cited by examiner

*Primary Examiner* — Sue Liu
*Assistant Examiner* — Thor Nielsen

(57) ABSTRACT

The present invention provides an agricultural pesticide formulation of reduced toxicity and high dispersibility, and a process for making the same.

6 Claims, No Drawings

AGRICULTURAL PESTICIDE FORMULATIONS AND PROCESS FOR MAKING THE SAME

BACKGROUND OF THE INVENTION

1. Field of the Invention

The present invention relates to pesticide compositions. In particular, the present invention relates to solid compositions containing a low-melting pesticide, such as Bifenthrin, further comprising carrier, surfactant and diluent, and optionally wetting agents, dispersing agents and formulation auxiliaries. This invention is particularly suitable in providing a solid pesticide composition having lower toxicity yet greater suspensibility and dispersion than previously known pesticide compositions.

2. Description of the Related Art

There are a large number of Bifenthrin formulations that are being used for combating pesticidal attacks on plants. Available formulations include emulsion concentrates, aqueous suspensions, and powder that is contained in water-soluble bags. Such formulations are widely available in market for a good number of years; however, the users have regularly encountered various technical difficulties with these available formulations.

Quality of a pesticide formulation is greatly dependent on its physicochemical properties. These physicochemical properties are significantly altered by factors such as moisture content in the final composition inter alia on the method of its drying, temperature, purity of the active contents and the raw material etc.

Disadvantageously, unsatisfactory non-uniform dissolution (dispersion) of the composition leads to lack of homogeneity in the resulting mixture and prevents distribution of constant concentration of the desired active in the fields. The use of water soluble bags to contain Bifenthrin powder so as to reduce its toxicity often leads to such undesirable dispersion. Because the dispersion is unsatisfactory, the less than optimal concentration of the active pesticide applied to the fields lead to waste of the pesticide, and risk increasing the resistance of insect pests to the pesticide.

Also, of the formulations available in the market some employ organic solvents, such as emulsions concentrates that contain petroleum-based solvents, causing nuisance to the environment.

Bifenthrin coated granules are also available in the market, which has a very low content of Bifenthrin, e.g., 0.2%, and are used for nursery and gardens due to the low content of the active. These granules are applied directly onto the ground. The granules then release the active overtime as it rains. The low content of bifenthrin preclude the use of this granular product for general agricultural applications.

Though there are different formulation types available in the market there is a need for a Bifenthrin solid composition of low toxicity that could packed and used without the use of water soluble bags, which overcomes one or more problem, faced in the art.

SUMMARY OF THE INVENTION

Accordingly, it is an object of the present invention to provide a pesticide compositions or formulations, which can have, in practice, a low toxicity that could be directly used upon mixing with water.

Another object of the present invention is to provide products of superior suspensibility and dispersion; and higher storage stability.

In accomplishing the forgoing objects, the present invention provides a granular compositions/formulations, which can be handled with ease, can flow easily, which are easy to measure out by volume, and leave no, or little residues in the emptied packaging after use.

The present invention provides for an agricultural pesticide formulation comprising:
- 0.1 to 99.7% by weight of carrier selected from the group consisting of precipitated silica, colloidal silica, attapulgite clay, china clay, talc, kaolin and combination thereof;
- 0.1 to 50.0% by weight of pesticide with a melting point between about 30° C. to about 85° C.;
- 0.1 to 25.0% by weight of surfactant; and
- 0.1 to 50.0% by weight of a diluent selected from the group consisting of lactose, glucose, fructose, maltose, sucrose, in the anhydrous or hydrate forms, urea, water soluble or dispersible polymers, water soluble inorganic salts and combination thereof.

The pesticide formulation may be in the form of granules. The pesticide may be bifenthrin, chloropyrifos, lambda-cyhalothrin, gama-cyhalothrin, trifluralin, pendimethalin, cypermethrin, alpha-cypermethrin, beta-cypermethrin and tefluthrin. The surfactant may be Atlox Metasperse 550 S, Tresperse 2700, Geropon SC-213, Morwet EFW, Supragil WP, Morwet D-425, lignin sulfonate salts or combination thereof. The pesticide formulation may also optionally contain a wetting and/or dispersing agent.

The present invention also provides for a process of producing an agricultural pesticide formulation comprising the steps of:

mixing a crystalline powder of a pesticide, with a melting point between about 30° C. to about 85° C., in a desired amount; a carrier selected from the group consisting of precipitated silica, colloidal silica, attapulgite, china clay, talc, kaolin and combination thereof, and a surfactant, and a diluent selected from the group consisting of lactose, glucose, fructose, maltose, sucrose, in the anhydrous or hydrate forms, urea, water soluble or dispersible polymers, water soluble inorganic salts and a combination thereof; to form a mixture;

milling the mixture until the particles are 75 microns or less in size preferably D100≤30; and D90≤15 µm adding water to wet the milled mixture;

extruding the wet milled mixture to form granules; and drying the granules below the melting point of the pesticide to produce the agricultural pesticide formulation.

This process is especially useful in producing a formulation containing bifenthrin, chloropyrifos, lambda-cyhalothrin, gama-cyhalothrin trifluralin, pendimethalin, cypermethrin, alpha-cypermethrin, beta-cypermethrin and tefluthrin.

The process optimally uses the surfactant Atlox Metasperse 550 S, Tresperse 2700, Geropon SC-213, Morwet EFW, Supragil WP, Morwet D-425, lignin sulfonate salts or combination thereof, and diluents selected from the group consisting of lactose, glucose, fructose, maltose, sucrose in anhydrous or hydrate forms, urea, water soluble or dispersible polymers, water soluble inorganic salts and combination thereof, to form a mixture. The process optimally requires the wetting of the milled mixture with water, in the amount of 5 to 50% of the milled mixture, preferably 10 to 15%. Further, the process optionally adds a wetting agent or dispersing agent or both to produce the pesticide formulation.

In one preferred embodiment, the present process of producing an agricultural pesticide formulation comprises the steps of:

providing a crystalline powder of a pesticide with a melting point between about 30° C. to about 85° C.;

mixing the crystalline powder of a pesticide with a carrier selected from the group consisting of precipitated silica, colloidal silica, attapulgite china clay, talc, kaolin and combination thereof to form a first mixture;

mixing a solid surfactant Atlox Metasperse 550 S, Tresperse 2700, Geropon SC-213, Morwet EFW, Supragil WP, Morwet D-425, lignin sulfonate salts or combination thereof into the first mixture to form a second mixture;

mixing a diluent selected from the group consisting of lactose, glucose, fructose, maltose sucrose, in the anhydrous or hydrate forms, urea, water soluble or dispersible polymers, water soluble inorganic salts and a combination thereof into the second mixture to form a third mixture;

milling the third mixture until the particles are 75 microns or less in size preferably D100≤30; and D90≤15 µm;

adding water to wet the milled third mixture;

extruding the wet milled third mixture to form granules; and drying the granules below the melting point of the pesticide to produce the agricultural pesticide formulation.

In one preferred embodiment, the present invention provides a formulation containing an insecticidally effective amount of bifenthrin active, a carrier such as precipitated silica, and kaolin, a surfactant component selected from Atlox Metasperse 550S, Tersperse 2700, Geropon SC-213, Morwet EFW and combinations thereof, a diluent component selected from lactose, glucose, fructose, maltose, sucrose, wherein these sugars are in the anhydrous or hydrate forms, urea, water soluble or dispersible polymers, water soluble inorganic salts or a combination thereof.

The compositions of the present invention provide low toxicity, increased suspensibility and dispersion over compositions of the prior art. The lower toxicity of the compositions results in less skin irritation and sensitization to the user. Specifically, the compositions have lower dermal toxicity compared to available commercial powder formulation of bifenthrin products such as Bifenthrin 10 WSB (without Lactose). Further, the compositions have lower acute oral and acute inhalation toxicity. The compositions of the present invention further provide greater storage stability.

DETAILED DESCRIPTION OF THE PRESENTLY PREFERRED EMBODIMENTS

An embodiment of the formulation of the present invention comprises bifenthrin active ingredient in a desired amount, a diluent, a surfactant and a carrier, optionally wetting agents and for dispersing agents. The optimal quality and the performance of the end product are greatly dependent upon the choice of the right ingredients used in the right proportion.

The present inventors have surprisingly found an unexpected reduction in the toxicity achieved by the use of a surfactants such as Atlox Metasperse 550S, Morwet EFW, diluent such as lactose and carrier such as precipitated silica and kaolin in the formulations according to the present invention.

It was found by the inventors that the combination of bifenthrin with a surfactant, a diluent, and carrier greatly reduces the toxicity without compromising on its suspensibility and dispersibility and its desired insecticidal activity.

The general pesticide composition of the present invention comprises (a) an insecticidally effective amount of a pesticide active component with a melting point of about 30 C. to about 85 C.;

(b) a surfactant;

(c) a diluent; and;

(d) a carrier.

The carrier may be precipitated silica, colloidal silica, attapulgite china clay, talc, kaolin or combination thereof, preferably precipitated silica and kaolin. The surfactants may be Atlox Metasperse 550 S, Tresperse 2700, Geropon SC-213, Morwet EFW, Supragil WP, Morwet D-425, lignin sulfonate salts or combination thereof preferably Atlox Metasperse 550 S and Morwet EFW. The diluents may be lactose, glucose, fructose, maltose, sucrose, in the anhydrous or hydrate forms, urea, water-soluble or dispersible polymers, water soluble inorganic salts or a combination thereof, preferably lactose. Diluents may be lactose, starch or combinations thereof. Lactose is most preferably used as the diluent. Without wishing to be bound by theory, it is believed that the carbohydrate sugar, such as lactose, acts as an in situ film forming or surface coating agent in the pesticide composition, coating the active and carrier. When the pesticide composition is extruded and dried in the form of granules, it is believed that the lactose form a coating on the granules. It is believed that the lactose coating contributes to the desired reduced toxicity of the pesticide composition, thus allowing the composition to be used without the need to be contained in water soluble bags or other packaging to avoid direct exposure to users.

Tests were conducted on granular formulations that contain 10% bifenthrin and various combinations of carrier (which appear to act as a solubility modulating agent), surfactants and diluents. Testing of the formulations showed that the low toxicity, superior suspensibility and dispersion, which were achieved by the granular formulations that contained specific combinations of surfactants, diluents and carriers.

| Toxicity Results: | | |
|---|---|---|
| | UPI Bifen 10 DF | Bifenthrin 10 WSB (without Lactose) |
| Acute Oral Tox | $LD_{50}$ 550 mg/kg | $LD_{50}$ 335 mg/kg |
| Acute Inhalation | $LC_{50}$ 5.869 mg/kg | $LC_{50}$ 3.35 mg/kg |

Using the methods described herein, the following exemplary formulations were prepared and tested. It should be understood however that the exemplary formulations described herein describe the invention for purposes of illustration only and are not intended to limit the scope of the appended claims or the invention in any manner.

Table I: Shows the Various Combination of Surfactants, Diluents and Carriers Tried to Form the Granular Product and the Gravimetric Suspensibility of Granules.

| Example No. | Active ingredient | Surfactants | Diluents | Carriers | Gravimetric suspensibility % by mass |
|---|---|---|---|---|---|
| 1 | Bifenthrin (98% purity) 10.71% | Geropon SC-213 10% | Morwet EFW 3% | Starch 46.5% | Kaolin 25.79% + precipitated silica 4.00% | 87.42 |
| 2 | Bifenthrin (98% purity) 10.71% | Geropon SC 213 10% | Morwet EFW 3% | Lactose 46.5% | Kaolin 25.79% + precipitated silica 4.00% | 90.25 |
| 3 | Bifenthrin (98% purity) 10.71% | Morwet D-425 10% | Morwet EFW 3% | Starch 46.5% | Kaolin 25.79% + precipitated silica 4.00% | 56.01 |
| 4 | Bifenthrin (98% purity) 10.71% | Morwet D-425 10% | Morwet EFW 3% | Starch 20% + lactose 26.5% | Kaolin 25.79% + precipitated silica 4.00% | 79.54 |
| 5 | Bifenthrin (98% purity) 10.71% | Atlox Metasperse 550 S 10% | Morwet EFW 3% | Lactose 46.5% | Kaolin 25.79% + precipitated silica 4.00% | 92.54 |
| 6 | Bifenthrin (98% purity) 10.71% | Atlox Metasperse 550 S 5% + Geropon SC-213 5% | Morwet EFW 3% | Lactose 26.5% + Starch 20% | Kaolin 25.79% + precipitated silica 4.00% | 90.28 |
| 7 | Bifenthrin (98% purity) 10.71% | Atlox Metasperse 550 S 10% | Morwet EFW 3% | Lactose 26.5% + Starch 20% | Kaolin 27.29% + precipitated silica 2.5% | 98.57 |
| 8 | Bifenthrin (98% purity) 10.71% | Atlox Metasperse 550 S 10% | Morwet EFW 3% | Lactose 26.5% + ammonium sulphate 20% | Kaolin 33.79% + precipitated silica 2.5% | 69.01 |
| 9 | Bifenthrin (98% purity) 10.71% | Atlox Metasperse 550 S 10% | Morwet EFW 3% | Ammonium sulfate 40% | Kaolin 33.79% + precipitated silica 2.5% | 64.55 |
| 10 | Bifenthrin (98% purity) 10.71% | Atlox Metasperse 550 S 10% | Morwet EFW 3% | Starch 20% + ammonium sulfate 20% | Kaolin 33.79% + precipitated silica 2.5% | 62.32 |
| 11 | Bifenthrin (98% purity) 16.33% | Atlox Metasperse 550 S 10% | Sodium lauryl sulfate 3% | Starch 56.67% | Kaolin 10.00% + precipitated silica 4.0% | 74.81 |
| 12 | Bifenthrin (98% purity) 16.33% | Atlox Metasperse 550 S 10% | Dispersol PS 3% | Starch 51.67% | Kaolin 15.00% + precipitated silica 4.0% | 45.08 |
| 13 | Bifenthrin (98% purity) 16.33% | Atlox Metasperse 550 S 10% | Supragil WP 3% | Starch 51.67% | Kaolin 15.00% + precipitated silica 4.0% | 67.8 |
| 14 | Bifenthrin (98% purity) 10.50% | Atlox Metasperse 550 S 10% | Morwet EFW 3% | Lactose 30% | Kaolin 43.82% + precipitated silica 2.50% | 95.23 |

Table II Shows the Results of Disintegration/Dispersibility in Terms of Number of Inversion Required to Completely Disintegrate the Granular Product, Produced by Using Compositions Listed in Table I Above.

| Number of inversion for complete disintegration | | |
|---|---|---|
| Example No. | At 30° C. | At 10° C. |
| 1 | 17 | 33 |
| 2 | 19 | 35 |
| 3 | 16 | 30 |
| 4 | 17 | 32 |
| 5 | 23 | 38 |
| 6 | 15 | 27 |
| 7 | 12 | 26 |
| 8 | 5 | 10 |
| 9 | 4 | 7 |
| 10 | 4 | 6 |
| 11 | 16 | 32 |
| 12 | 18 | 32 |
| 13 | 16 | 30 |
| 14 | 10 | 19 |

It can be seen from Table I and II that the compositions of the present invention exhibit superior disintegration/dispersibility even at a temperature as low as 10° C. It is evident from the above test results that good suspensibility and dispersion is achieved by the formulations containing specific combinations of diluent, surfactant and carriers. From the above table it is concluded that the example no. 7, 8, 9, 10 and 14 are found to be the best out of the compositions mentioned in the Table I.

Table III Shows the Results of Suspensibility of Certain Best Examples Out of Table I and II, to Ascertain the Better Suspensibility of the Granular Product by Accelerated Heat Stability Treatment "AHS" (at 54±2° C. For the Period of 14 Days)

| Example No. | Suspensibility by active content determination (% by mass) at 54 ± 2° C. | | Gravimetric suspensibility (% by mass) at 54 ± 2° C. | |
|---|---|---|---|---|
| | Before AHS | After AHS | Before AHS | After AHS |
| 7 | 67.04 | 64.22 | 71.60 | 61.00 |
| 8 | 62.85 | 55.11 | 69.04 | 63.76 |
| 9 | 59.32 | 52.47 | 64.29 | 56.44 |
| 10 | 73.55 | 67.88 | 77.29 | 70.86 |
| 14 | 90.36 | 88.45 | 95.26 | 93.76 |

CONCLUSION

It is apparent from the Table III, that the example no. 14 maintains the suspensibility to a greater extent (minimum 95% of that before AHS test) when compared to example 7, 8, 9 and 10, though example 7 and 10 fulfills the criteria of minimum 60% suspensibility in AHS study.

The process of the present invention was employed to prepare a preferred formulation as concluded in Table III, which is not the limiting one and it is intended to illustrate an exemplary embodiment of the invention.

Composition:—

| S No. | Ingredient | Quantity (in g) |
|---|---|---|
| 1 | Bifenthrin technical (98%) | 10.50 |
| 2 | Precipitated silica | 02.50 |
| 3 | Atlox Metasperse 550 S | 10.00 |
| 4 | Morwet EFW | 3.00 |
| 5 | Lactose | 30.00 |
| 6 | Kaolin (q.s.) | 43.82 |
| | Total | 100.00 g |

The above composition was prepared by the following process of producing an agricultural pesticide formulation comprises the steps of:

Mixing the 10.50 g of Bifenthrin technical with 2.50 g of precipitated silica and grinding it and blending to form a first mixture; thereafter adding 10.00 g of Atlox Metasperse 550 S and 3.0 g of Morwet-EFW to the first mixture to form a second mixture; then 30.0 g of Lactose and 43.82 g of Kaolin were mixed with the second mixture to form a third mixture; milling the third mixture until the particles are 75 microns or less in size preferably D100≤30; and D90≤15 μm; adding 12.28 g water to wet the milled third mixture; extruding the wet milled third mixture to form granules; and drying the granules below the melting point of the pesticide to produce the agricultural pesticide formulation.

For the illustration purpose we have given examples of the Granular formulation only. This invention may be embodied in other forms also without departing from the essential characteristics thereof. Thus, the present embodiments should be considered as illustrative only and does not restrict, in any way, the scope of the invention.

The invention claimed is:

1. An agricultural pesticide formulation comprising:
   2.5% by weight of precipitated silica;
   43.82% by weight of kaolin;
   10.5% by weight of bifenthrin;
   13% by weight of at least one surfactant; and
   30% by weight of lactose.

2. The formulation of claim 1 is in the form of granules.

3. The formulation of claim 1 wherein the surfactant is selected form the group consisting of styrene acrylic dispersant polymers, acid resin copolymer based dispersing agents, potassium polycarboxylate, sodium alkyl naphthalene sulfonate blend, sodium diisopropylnaphthalenesulfonate, sodium salt of naphthalene sulfonate condensate, lignin sulfonate salts and combination thereof.

4. A process of producing an agricultural pesticide formulation of claim 1 consisting essentially of the steps of:
   a) mixing bifenthrin in powder form with precipitated silica and kaolin to form a first mixture;
   b) mixing the surfactant with the first mixture to form a second mixture;
   c) mixing the lactose with the second mixture to form a third mixture;
   d) milling the third mixture until the particles are 75 microns or less in size;
   e) adding water to the product of step d) and extruding the wet product of step d) to form granules; and
   f) drying the granules below the melting point of the pesticide to produce the agricultural pesticide formulation.

5. The process of claim 4 wherein the surfactant is selected from the group consisting of styrene acrylic dispersant polymers, acid resin copolymer based dispersing agents, potassium polycarboxylate, sodium alkyl naphthalene sulfonate blend, sodium diisopropylnaphthalenesulfonate, sodium salt of naphthalene sulfonate condensate, lignin sulfonate salts and combination thereof.

6. The process of claim 4 wherein the third mixture is milled until the particles size satisfies the following requirement: D100≤30 μm; and D90≤15 μm.

* * * * *